US011337831B2

(12) United States Patent
Nino (10) Patent No.: US 11,337,831 B2
(45) Date of Patent: May 24, 2022

(54) FLEXIBLE RADIOPAQUE TRIAL, PLATE AND METHOD OF USE

(71) Applicant: ECA Medical Instruments, Thousand Oaks, CA (US)

(72) Inventor: John Nino, Simi Valley, CA (US)

(73) Assignee: ECA Medical Instruments, Inc., Thousand Oaks, CA (US)

( * ) Notice: Subject to any disclaimer, the term of this patent is extended or adjusted under 35 U.S.C. 154(b) by 0 days.

(21) Appl. No.: 16/397,766

(22) Filed: Apr. 29, 2019

(65) Prior Publication Data

US 2019/0247203 A1   Aug. 15, 2019

Related U.S. Application Data

(63) Continuation of application No. PCT/US2017/058741, filed on Oct. 27, 2017.

(Continued)

(51) Int. Cl.
*A61B 17/70*   (2006.01)
*A61B 17/80*   (2006.01)
(Continued)

(52) U.S. Cl.
CPC ........ *A61F 2/4684* (2013.01); *A61B 17/1728* (2013.01); *A61B 17/7059* (2013.01); *A61B 17/8004* (2013.01); *A61B 17/808* (2013.01); *A61B 17/8061* (2013.01); *A61F 2/30* (2013.01); *A61F 2/4455* (2013.01); *A61F 2/4465* (2013.01); *A61F 2/4611* (2013.01); *A61B 17/1757* (2013.01); *A61B 17/1782* (2016.11);
(Continued)

(58) Field of Classification Search
CPC ........ A61F 2/4684; A61F 2/30; A61F 2/4455; A61F 2/4465; A61F 2/4611; A61F 2/4603; A61F 2002/3008; A61F 2002/30616; A61F 2002/4629; A61B 17/1728; A61B 17/7059; A61B 17/8004; A61B 17/8061; A61B 17/808; A61B 17/1782; A61B 17/1757; A61B 2090/3966; A61L 31/18; A61L 2430/02
USPC ........ 606/86 R, 866, 98–100, 102, 246–289; 623/17.11–17.16
See application file for complete search history.

(56) References Cited

U.S. PATENT DOCUMENTS 4,959,065 A   9/1990   Arnett
5,438,242 A   8/1995   Simpson
(Continued)

FOREIGN PATENT DOCUMENTS

WO      2014158680      10/2014
WO   WO 2016/073753 A1   5/2016

OTHER PUBLICATIONS

"ULTEM™ RESIN"; https://www.sabic.com/en/products/speciaities/ultem-resins/ullem-resin; accessed Dec. 4, 2017; 22 pages.
(Continued)

*Primary Examiner* — Pedro Philogene
(74) *Attorney, Agent, or Firm* — Ferguson Case Orr Paterson (57) ABSTRACT

A flexible plastic, resin or polymer material forming a trial plate for use is surgery of bones including spine and extremities. The trial plate having at least one radio opaque region and guides for positioning. A kit may be provided containing at least one flexible trial plate.

18 Claims, 7 Drawing Sheets

Related U.S. Application Data (60) Provisional application No. 62/413,896, filed on Oct. 27, 2016.

(51) Int. Cl.

| | | |
|---|---|---|
| *A61F 2/46* | (2006.01) | |
| *A61F 2/44* | (2006.01) | |
| *A61B 17/17* | (2006.01) | |
| *A61F 2/30* | (2006.01) | |
| *A61B 90/00* | (2016.01) | |
| *A61L 31/18* | (2006.01) | |

(52) U.S. Cl.
CPC ..... *A61B 2090/3966* (2016.02); *A61F 2/4603* (2013.01); *A61F 2002/3008* (2013.01); *A61F 2002/30616* (2013.01); *A61F 2002/4629* (2013.01); *A61L 31/18* (2013.01); *A61L 2430/02* (2013.01)

(56) References Cited

U.S. PATENT DOCUMENTS

| | | | |
|---|---|---|---|
| 5,468,242 | A | 11/1995 | Reisberg |
| 6,206,882 | B1 | 3/2001 | Cohen |
| 6,506,191 | B1 | 1/2003 | Joos |
| 6,656,181 | B2 | 12/2003 | Dixon |
| 7,077,844 | B2 | 7/2006 | Michelson |
| 7,247,169 | B1 | 7/2007 | Lo |
| 8,118,847 | B2 | 2/2012 | Wallenstein |
| 8,133,282 | B2 | 3/2012 | Hushka |
| 2005/0027300 | A1 | 2/2005 | Hawkins et al. |
| 2005/0085814 | A1 | 4/2005 | Sherman |
| 2006/0116679 | A1 | 6/2006 | Lutz et al. |
| 2008/0091199 | A1 | 4/2008 | Cragg |
| 2010/0234895 | A1 | 9/2010 | Hess |
| 2011/0218570 | A1* | 9/2011 | Felix .............. A61L 31/18 606/246 |
| 2014/0163621 | A1* | 6/2014 | Huebner .......... A61B 17/1782 606/281 |
| 2014/0180339 | A1 | 6/2014 | Ritland |
| 2015/0313652 | A1 | 11/2015 | Burckhardt |
| 2017/0020683 | A1* | 1/2017 | Bray, Jr ............ A61F 2/4465 |
| 2017/0042593 | A1* | 2/2017 | Newman ............ A61L 31/18 |
| 2018/0235778 | A1 | 8/2018 | Nino |

OTHER PUBLICATIONS

International Patent Application No. PCT/US2017/58741; Int'l Search Report and the Written Opinion; dated Jan. 12, 2018; 11 pages.

International Patent Application No. PCT/US2017/058741; Int'l Preliminary Report on Patentability; dated May 9, 2019; 10 pages.

Anonymous, "ULTEM Resin", SABIC, (Dec. 4, 2017), pp. 1-35, URL: https://www.sabic.com/en/products/speciaities/ultem-resins/ultem-resin, XP055593993.

International Patent Application No. PCT/US2015/059290; Int'l Preliminary Report on Patentability; dated May 18, 2017; 9 pages.

International Search Report and Written Opinion dated Feb. 17, 2016 in International Patent Application No. PCT/US2015/029290.

* cited by examiner

FLEXIBLE RADIOPAQUE TRIAL, PLATE AND METHOD OF USE

CROSS REFERENCE

This application is a Continuation of International Patent Application No. PCT/US2017/058741 filed Oct. 27, 2017, which claims priority to U.S. Provisional Patent Application 62/413,896 filed Oct. 27, 2016, the contents of which are incorporated herein by reference as if fully set forth herein.

BACKGROUND

1. Field

This disclosure relates to a kit of disposable devices for assessment of positioning of implants, fixing devices such as screws and bone plate systems or connection devices.

2. General Background

Treating bone injuries may require the surgeon to remove diseased or damaged bone such as disc and utilize spacer or inserts in combination with plates, screws, cages and the like to affix adjacent vertebra together. For extremity repair of a bone such as the distal radius a plate is affixed to maintain the surgeon set or optimal set position during the bone healing period.

DISCLOSURE

Briefly stated, kits providing swappable disposable radiopaque spinal disc spacers or inserts of various sizes and an instrument to insert and remove, "swap", the spacers are disclosed. The inserts may be partially radiolucent and partially radiopaque to facilitate visualization under X-rays/fluoroscope. The trial plate may be partially radiolucent and partially radiopaque to facilitate visualization under X-rays/fluoroscope. At least two inserts of varying sizes are supplied with a kit. In some instance the trial plates are flexible.

Aspects of implementations include kits containing one or more of a flexible plastic, resin or polymer trial plates for use is surgery of bones including spine and extremities. The trial plate having at least one radio opaque region and guides for positioning. In a kit trial plates of varying sizes may be provided to customize the trial.

Aspects of implementations include kits comprising one or more flexible trial plates formed of a flexible plastic material; at least one of the trial plates at least partially radiopaque; and, one or more guides are provided. In some instances the one or more guides are at least one of positioning guides and edge markers; and, each having at least some radiopaque portions. In some instances the positioning guides are surrounded by radiopaque guide regions. In some instances the at least one trial plate comprises at least one radiolucent region.

Aspects of implementations include kits comprising one or more flexible trial plates formed of a flexible plastic material; at least one of the trial plates at least partially radiopaque; and, one or more guides are provided wherein the at least one flexible trial plate is coated with a radiopaque material. In some instances at least two of the flexible trial plates have different size, shape, or both relative to each other.

In some instance the kits have a portion of each of the flexible trial plates radiolucent or radiopaque.

Aspects of implementations include a trial plate formed of a flexible plastic material; the trial plate is at least partially radiopaque; and, at least one of edge markers and guides are provided thereon. In some instances the at least two guides are a positioning guides surrounded by radiopaque guide regions. In some instances the edge markers are at least partially radiopaque.

Aspects of implementations and methods include providing a flexible trial plate configured whereby when positioned over an extremity such as a Radius and/or Ulna at least a portion of a radius is visible, under X-rays or fluoroscope, through the radiolucent region.

DRAWINGS

The above-mentioned features of the present disclosure will become more apparent with reference to the following description taken in conjunction with the accompanying drawings wherein like reference numerals denote like elements and in which.

As shall be appreciated by those having ordinary skill in the art, the figures are not to scale, and modifications to scale within a figure or across the figures are considered within the present disclosure.

FURTHER DESCRIPTION

Being disposable and single use the kit parts described herein avoid exposure of patients to radiopaque materials used herewith for all but a brief exposure. Further, the coating on coated embodiments may be extremely thin, to again limit the amount of such materials used or exposed to humans, due to the disposable nature of the kit parts.

Figure 1A:
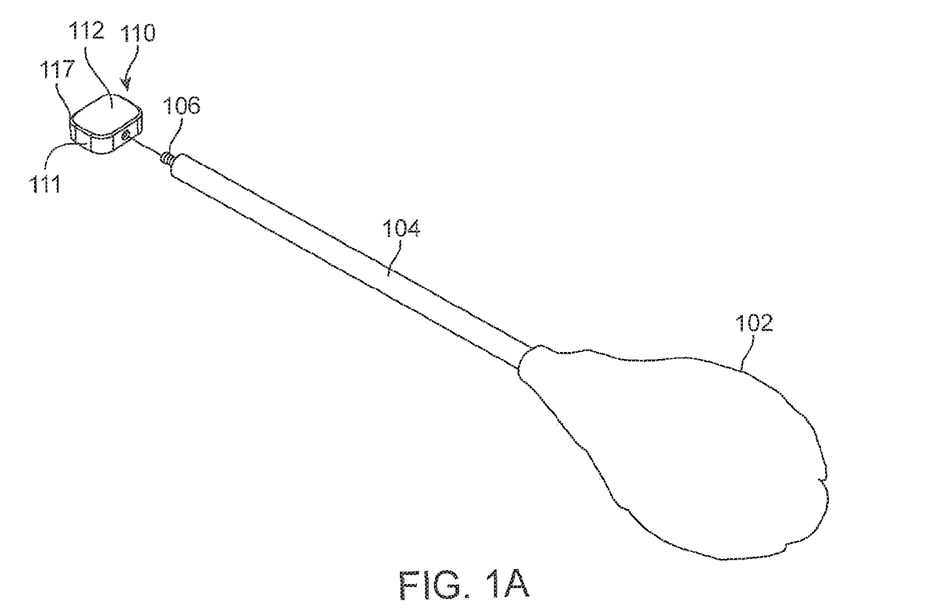
FIGS. 1A-1C are disc insert and tool.
Figure 1B:
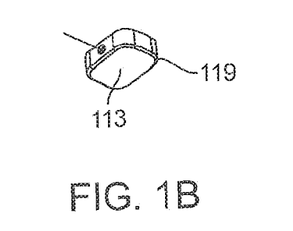
Figure 1C:
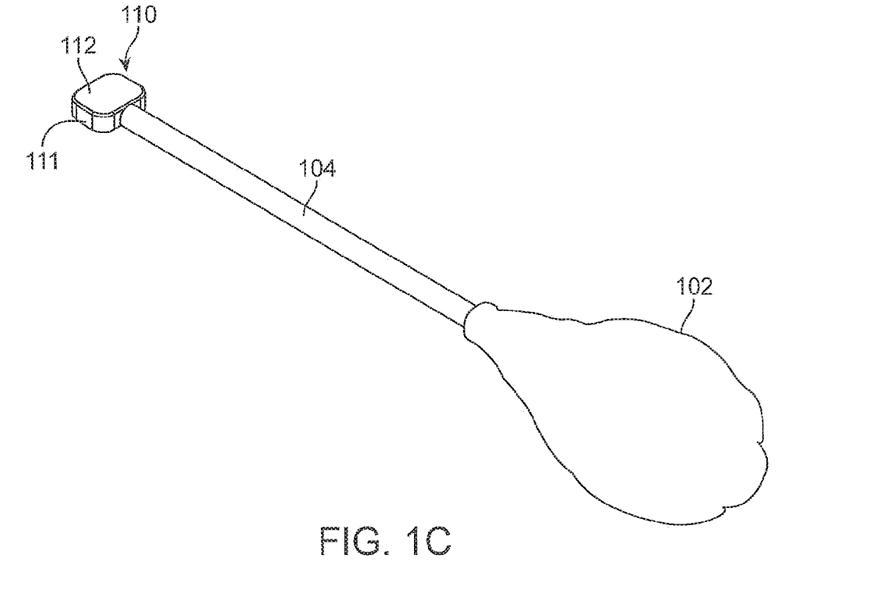

FIGS. 1A-1C show a tool 100 having a handle 102 for grasping and a shaft 104 affixed to the handle at one end and a free end 105 having a threaded connection 106. An insert 110 is disclosed of a size to approximate an intervertebral space. A kit may contain a plurality of inserts of varying sizes to give a surgeon choice in selecting the insert which best approximates an intervertebral space. The insert 110 is roughly a rounded square having an annular wall 111 surrounding a top surface 112 and a bottom surface 113. A threaded catch 115 is formed in the insert to mate with the threaded connection 106. The interface between the disc insert, top surface, and annular wall 111 forms a first perimeter 117 and the interface between the disc insert bottom surface and the annular wall 111 forms a second perimeter 119.

FIGS. 1A-6C show aspects of exemplary implementations of devices, methods and system which may include a kit with inserts 110 of various sizes. The inserts can be formed of plastic having radiopaque material therein. The insert may be coated with a radiopaque material or marker on one or more of a top surface 112, a bottom surface 113, an annular wall 111 and a perimeter 117/119. In some instances the insert may have radiolucent regions 120 or portions and radiopaque portions or regions 122.

Figure 2:
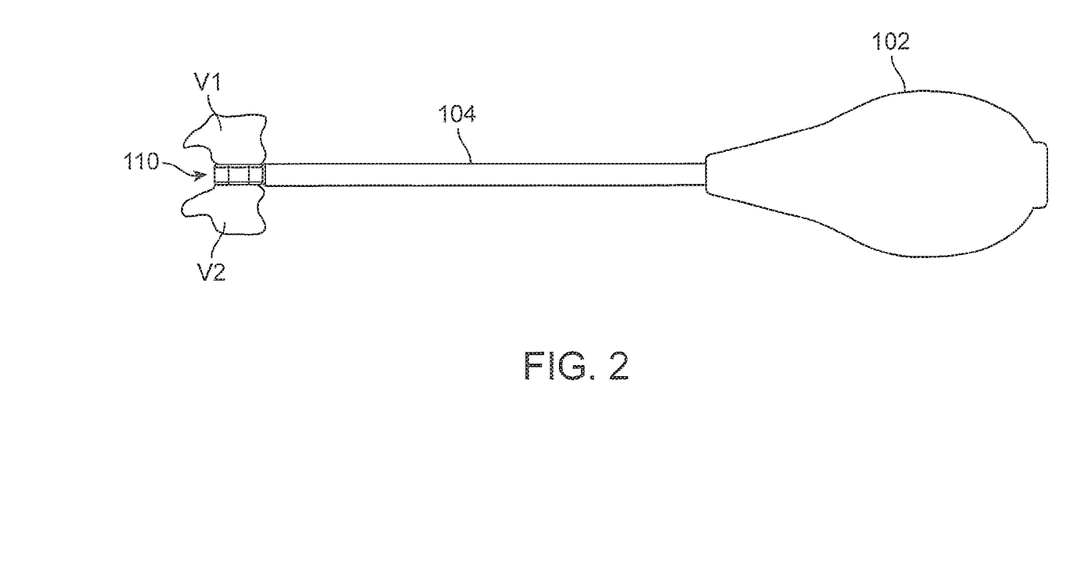
FIG. 2 shows a tool inserting a disc insert.
Figure 3:
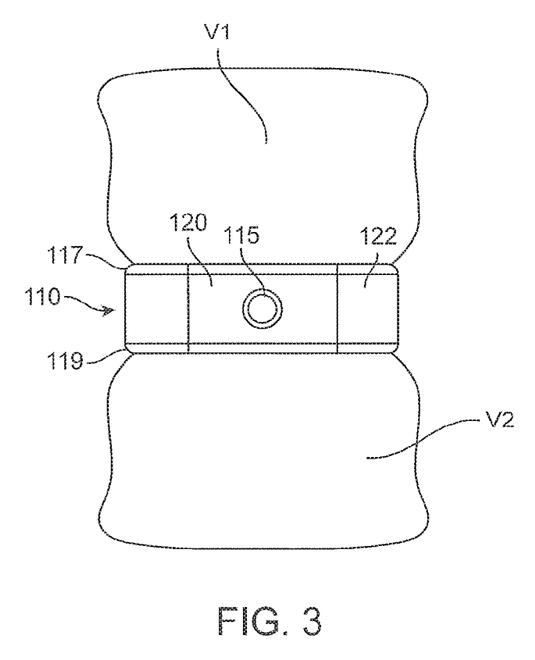
FIG. 3 shows a disc insert between vertebra.

When the tool 100 is connected to the insert 110, the insert is then inserted between a top vertebra "V1" and a bottom vertebra "V2".

A system and method of use includes a kit with various size and thickness inserts 110 each connectable to the tool. The surgeon assesses the physical space for an insert and tries various inserts to ascertain the right size for an implantable device. After assessing the size and height of the insert, which can include visualization of the insert between an upper vertebra and a lower vertebra via at least one radiopaque region 122, radiopaque coating or marker. After the size and shape for the spinal final spinal disc spacer device (not shown) is assessed the insert is removed and replaced with a disc insert (not shown).

The insert 110 may have perimeters 117/119 and either perimeter, or a portion thereof, may be formed of or coated with a radiopaque material.

Figure 4:
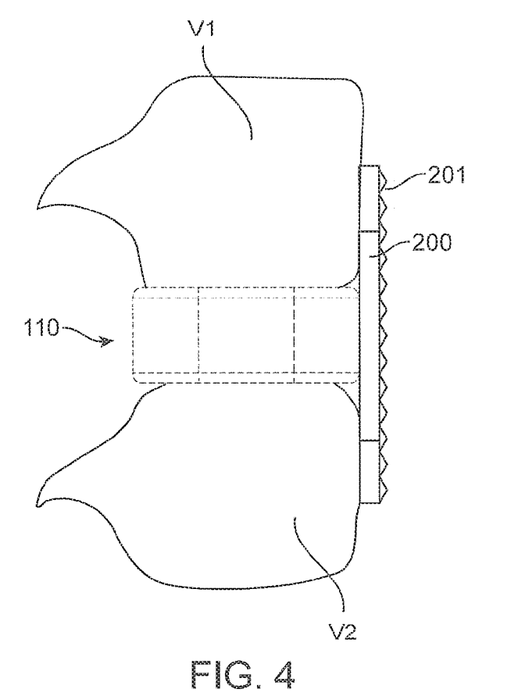
FIG. 4 shows a trial plate and disc insert.

A trial plate 200 also disclosed. A trial plate mimics the size and shape of a plate, cage or other device used in spinal fusion procedures. Part of the kit may include different sized trial plates. The trial plate may be coated 201 with a radiopaque material.

Figure 5A:
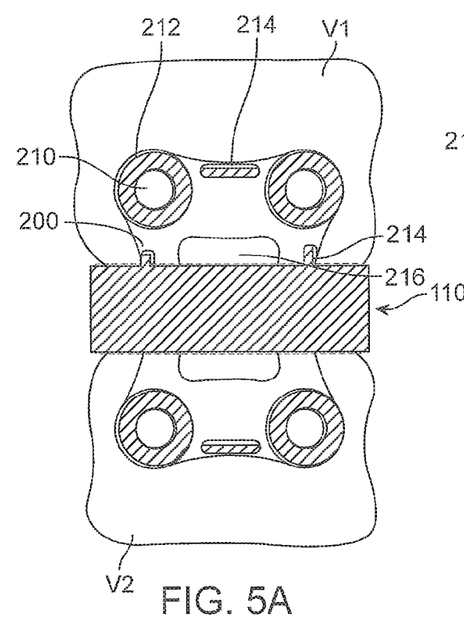
FIGS. 5A-5C shows aspects of radiopaque or marked trial plates and an insert; and,
FIGS. 6A-6C show diagrams of the distal radius of a hand and flexible radiopaque trial plate.

FIGS. 5A-6C show aspects of trial plate and insert combinations with varying radiopaque portions. Trial plates provide positioning guides 210 for the placement of drills, drill guides or fasteners (such as screws) for affixing a stabilizing device to vertebra during spinal fusion procedures. However, vertebra size and shape vary and a kit having multiple plates and/or inserts to choose from allows a surgeon to customize the fit to the patient. Having flexibility in the plate material further aids the surgeon in fit. In some instances radiopaque guide regions 212 surround positioning guides 210. In some instances radiopaque edge markers 214 are formed at the edges of the trial plate. In some instances radiolucent regions 216 are also provided on the trial plate. In FIG. 5A the insert 110 is radiopaque and visible through the radiolucent portion 216 of the trial plate 200.

Figure 5B:
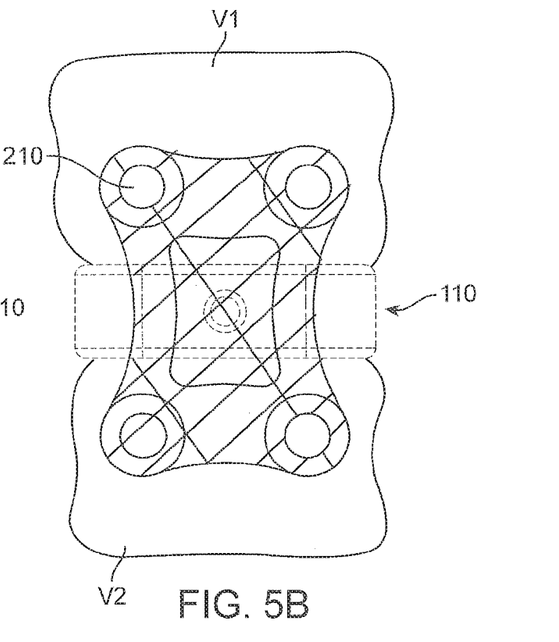
Figure 5C:
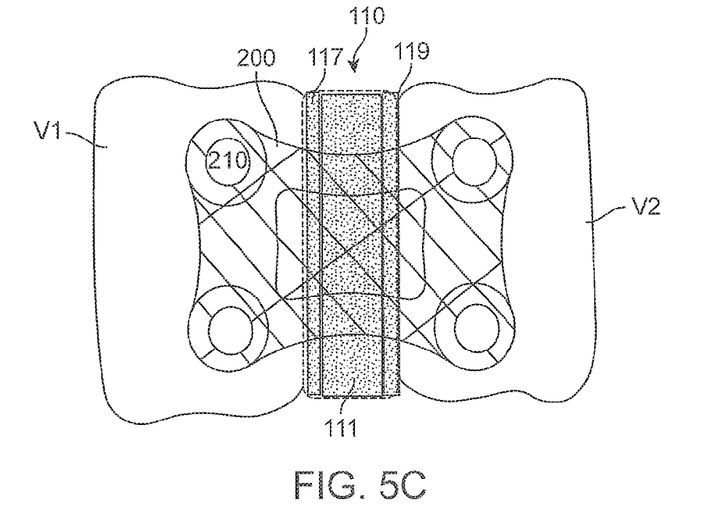

In FIG. 5B the trial plate is radiopaque except for the positioning guides 210. In FIG. 5C the trial plate 200 is radiopaque, but less radiopaque then the insert 110 or portions thereof.

Figure 6A:
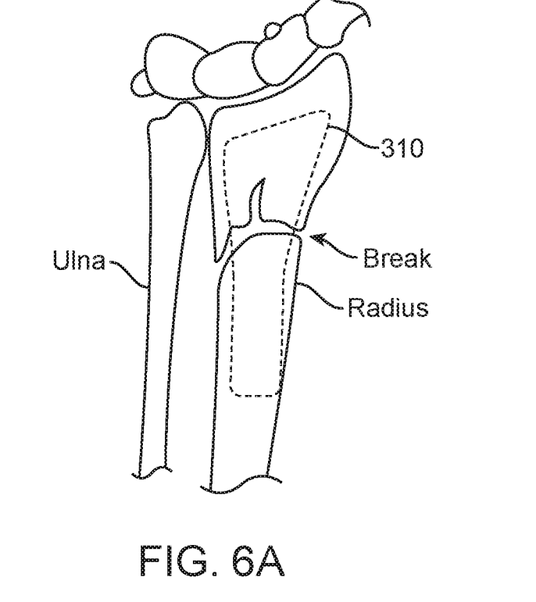
Figure 6B:
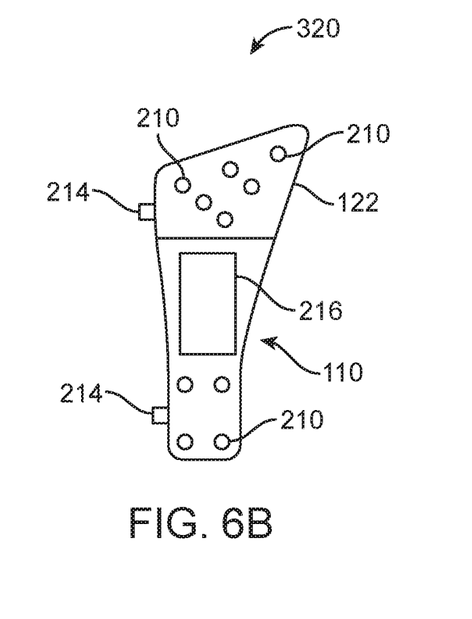
Figure 6C:
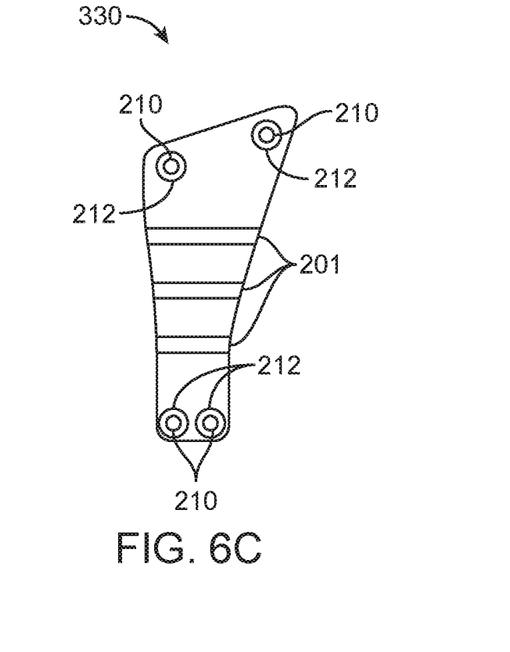

In FIGS. 6A-6C illustrate a partial diagram of an arm/hand extremity and aspects of flexible radiopaque trial plates. FIG. 6A is a system overview of a flexible radiopaque trial plate and extremity 300. The Ulna and Radius are shown in conjunction with a flexible at least partially radiopaque trial plate 310. FIGS. 6B and 6C illustrate additional flexible at least partially radiopaque trial plates 320 and additional device 330 showing the placement of positioning guides, radiopaque and radio translucent material and/or coating on flexible trial plates and associated methods of use as described in references to FIGS. 4-5C. In use, the radius, or a portion thereof, is visible under fluoroscope or X-ray through said radiolucent region 216.

By selection of concentrations of the radiopaque materials the insert or trial plate may be made distinguishable from the other. In some implementations, suitable materials for the insert or trial plate may include thermocomp (compound EX06430H from material manufacturer: Sabic Innovative Plastics, 1. Plastics Avenue Pittsfield, Mass. 01201), which may include barium sulfate and ULTEM' polyetherimide resin; other suitable materials can include tantalum, gold, platinum, iridium, palladium, and rhodium and are well recognized for their biocompatibility. Radiopaque coatings can be applied to plastics using a high-vacuum deposition process that results in dense thin-film coatings (typically less than 10 μm) that adhere to the surface of the device.

One or more of Barium Sulfate ($BaSO_4$), Bismuth Subcarbonate ($Bi_2O_2(CO_3)$), Bismuth Oxychloride (BiOCl), Bismuth Trioxide ($Bi_2O_3$), Barium or any salt thereof: e.g., barium aluminate, barium carbonate, barium hydroxide, barium oxide, barium fluoride, barium sulfide, barium titanate and Tungsten (W) may be used to provide radiopacity to one or more inserts or trial plates in some implementations. Radiopaque materials may be combined with and mixed into materials used for injection molding and thereby distributed throughout at least a portion of a device so manufactured.

Additional radiopaque materials include iodine or salt thereof; organic iodine molecules used for contrast include iohexol, iodixanol, ioversol, diatrizoic acid [(or its anionic form, diatrizoate), also known as amidotrizoic acid, or 3,5-diacetamido-2,4,6-triiodobenzoic], Iothalamate (used as the meglumine or sodium salt, or a combination), Ioxaglate (Ioxaglic acid (trade name Hexabrix)). They also include lead and lead salts and they include Bismuth compounds, such as bismuth trioxide, bisthmuth subcarbonate, and bismuth oxychloride.

Additional radiopaque materials include alloys of transition metals, especially Cr and Co, but also including Ag, Au, Cd, Hf, In, Ir, La, Mo, Nb, Os, Pd, Pt, Re, Rh, Ru, Pd, Sb, Sn, Ta, Te, V, W, and Zr.

Alloys comprising Co, Cr, Mo, Ni may be used as radiopaque coatings or additives. In some instances the plastic, resin or polymer base material contains or is coated with contains one or more of about 10% to 14% Cr; about 7% to 10% Ni; about 0.5% to 6% Mo; up to about 9% Co; about 0.5% to 4% Cu; and may include trace amounts of Al and Ti.

In some instances the flexible plastic, resin or polymer base material contains or is coated with contains one or more of chromium 12-20 wt %; Molybdenum 4 max. Tungsten 6 max. Cobalt 5-12 Iron 14 max.

In some instances the flexible plastic, resin or polymer base material contains or is coated with contains stainless steel, nitinol, tantalum, MP35N alloy, platinum, titanium.

In some instances the flexible plastic, resin or polymer base material contains or is coated with contains chromium; vanadium; molybdenum; cobalt; titanium; aluminum; zirconium; silicon; and nickel.

In some instances the flexible plastic, resin or polymer base material contains or is coated with contains nickel-cobalt-chromium alloy.

In some instances the flexible plastic, resin or polymer base material contains or is coated with contains nickel-cobalt-chromium-molybdenum alloy.

In some instances the flexible plastic, resin or polymer base material contains or is coated with contains chromium, and further containing molybdenum, nickel, cobalt, and tungsten, and minor amounts of at least one of aluminum, niobium, titanium and vanadium.

In some instances the flexible plastic, resin or polymer base material contains or is coated with contains nickel-titanium alloy including a ternary element selected from the group consisting of iridium, platinum, gold, rhenium, tungsten, palladium, rhodium, tantalum, silver, ruthenium and halfnium.

In some instances the flexible plastic, resin or polymer base material contains or is coated with contains nitinol, titanium, titanium-vanadium-aluminum alloy, cobalt-chromium alloy, cobalt-chromium-molybdenum alloy, cobalt-nickel-chromium-molybdenum alloy, biocompatible stainless steel, tantalum, niobium, hafnium, tungsten.

In some instances the flexible plastic, resin or polymer base material contains or is coated with contains stainless steel, nitinol, cobalt-chromium-nickel-molybdenum-iron alloy, or cobalt-chrome alloy or chonichrome.

In some instances the flexible plastic, resin or polymer base material contains or is coated with a cobalt alloy comprising from 26 to 30 weight percent chromium, from 5 to 7 weight percent molybdenum, up to 1.0 nickel, up to 0.75 iron, up to 1.0 manganese, and greater than 50 weight percent cobalt.

In some instances the flexible plastic, resin or polymer base material contains or is coated with a radiopaque cladding layer selected from the group consisting of platinum, gold, tantalum, tungsten, a platinum-iridium alloy, and palladium.

In some instances the flexible plastic, resin or polymer base material contains or is coated with an alloy comprising, by weight: a) at least about 23% nickel; b) greater than 8% to about 17% molybdenum; c) greater than about 30% of a combination of chromium and molybdenum; d) from zero to about 5% cobalt; and e) greater than zero to about 50% iron.

In some instances the flexible plastic, resin or polymer base material contains or is coated with an alloy comprising iron, chromium, and a first element selected from a group consisting of platinum, ruthenium, palladium, iridium, rhodium, gold, and osmium, the alloy having less than about 0.03% by weight of nickel and having a radiopacity greater than the radiopacity of UNS S31673.

In some instances the flexible plastic, resin or polymer base material contains or is coated with at least 40% by weight of iron, from about 5% by weight to about 20% by weight of chromium, and greater than about 5% by weight of a first element having a density greater than 9.9 g/cc, the alloy having less than or equal to 1% by weight of nickel and having a radiopacity greater than the radiopacity of UNS S31673.

In some instances the flexible plastic, resin or polymer base material contains or is coated with a non-magnetic alloy comprising at least 40% by weight of iron, between about 5% and about 30% by weight of chromium, less than about 3% by weight of molybdenum, less than about 55% by weight of cobalt, less than about 20% by weight of manganese, less than about 6% by weight of copper, less than about 0.03% by weight of nickel, less than about 1.0% by weight of nitrogen, and between about 0.5% and about 40% by weight of a first element selected from a group consisting of platinum, ruthenium, palladium, iridium, rhodium, gold, and osmium, the alloy being substantially austenitic.

In some instances the flexible plastic, resin or polymer base material contains or is coated with a nonmagnetic nickel-cobalt-chromium-molybdenum [MP35N] alloy, platinum, titanium, a suitable biocompatible alloy, a suitable biocompatible material, and a combination thereof.

In some instances the flexible plastic, resin or polymer base material contains or is coated with alloy consists essentially of: from about 26 to about 28 weight percent chromium; from about 5 to 6 weight percent molybdenum; up to about 1 weight percent manganese; up to about 1 weight percent nickel, up to about 0.75 weight percent iron; up to about 0.07 weight percent carbon.

In some instances the flexible plastic, resin or polymer base material contains or is coated with a cobalt-chromium alloy comprising by weight percent: about 60 to about 85% cobalt; about 15 to about 30% chromium; about 4 to about 20% manganese; and about 1 to about 15% Al, In, GA, Sn, or Ge, or mixture thereof; optionally further comprising up to about 20% Fe, Ni, Pd, or Pt, or mixture thereof; up to about 10% gold; up to about 15% Ta, Nb, Mo, W, or V or mixture thereof; up to about 6% Ir, Ru, Re, Ti, Si or Cu or mixture thereof; and up to about 5% Zr, Hf, B, Y, or a rare earth metal or mixture thereof.

In some instances the flexible plastic, resin or polymer base material contains or is coated with a cobalt-chromium dental alloy comprising by weight percent: about 65 to about 80% cobalt; about 18 to about 25% chromium; about 4 to about 10% manganese; about 2 to about 10%, iron, nickel, palladium, or platinum, or mixture thereof; about 1 to about 7% Al, In, Ga, Sn, or Ge, or mixture thereof; about 1 to about 5% gold; and about 0.1 to about 3% Ir, Rum Re, Ti, Si, or Cu, or mixture thereof; optionally further comprising up to about 5% Ta, Nb, Mo, W, or V, or mixture thereof, and up to about 1% Zr, Hf, B, Y, or a rare earth metal, or mixture thereof.

In some instances the flexible plastic, resin or polymer base material contains or is coated with a metal selected from the group consisting of platinum, gold, tantalum, tungsten, platinum-iridium and palladium.

In some instances the flexible plastic, resin or polymer base material contains or is coated with stainless steel 316L, nitinol, a cobalt-chromium alloy, and other materials of similar radiopacity, plus an metal selected from the group comprising gold, gold alloys, tantalum, tantalum alloys, platinum, platinum alloys and other materials of similar radiopacity including 316 stainless steel, MP35N alloy, and 35NLT alloys; L-605 chromium-cobalt-tungsten-nickel alloys (nominally 19-21 wt % Cr, 14-16 wt % W, 9-11% Ni).

To make the insert or trial plate distinguishable from the other the perimeter 117/119 may be radiopaque and the edge or annular wall 11 not, or vice versa. Or the perimeters may be more radiopaque than the trial plate 200, 310, 320, 330 or portions thereof.

Additional suitable materials for an insert or flexible trial plate base material (which is then coated with or has incorporated into a radiopaque material as previously mentioned) may include polypropylene (i.e., polyolefins, including polyethylene, polypropylene, polybutylene, etc.), polyacrylate or methacrylates, polyalkyl (meth)acrylates), polypropylene sulfides, polybutylene terephthalates (including polyalkylene terephthalates or naphthalates). Pegylated copolymers, including pegylated styrenic block copolymer matrices; Polyurethanes, poly (N-vinylpyrrolidones), polycarbonates, polyphenylene oxides, polysiloxanes, phenoxy and epoxy resins. Additional compounds include synthetic polymers include, but are not limited to, aliphatic polyesters, poly (amino acids), copoly (ether-esters), polyalkylenes oxalates, polyamides, tyrosine derived polycarbonates, poly (iminocarbonates), polyorthoesters, polyoxaesters, polyamidoesters, polyoxaesters containing amine groups, poly(anhydrides), polyphosphazenes, polysiloxanes, and combinations thereof. More specifically, biosynthetic polymers based on sequences found in poly(amino acid), poly (propylene fumarate), polyethylene, polyethylene terephthalate, poly(tetrafluoroethylene), polycarbonate, polypropylene and poly(vinyl alcohol), and combinations thereof. Examples of biodegradable polymers include aliphatic polyesters, poly (amino acids), polyalkylene oxalates, polyamides, polyamido esters, poly (anhydrides), poly (beta-amino esters), polycarbonates, polyethers, polyorthoesters, polyphosphazenes, and combinations. More specific examples of biodegradable polymers include, but are not limited to, collagen (e.g., Collagen I or IV), fibrin, hyaluronic acid, polylactic acid (PLA), polyglycolic acid (PGA), polycaprolactone (PCL), poly (Lactide-co-Glycolide) (PLGA), polydioxanone (PDO), trimethylene carbonate (TMC), polyethyleneglycol (PEG), Collagen, PEG-DMA, or copolymers or mixtures thereof. Examples of nonbiodegradable polymers include, but are not limited to, carbon, nylon, silicon, silk, polyurethanes, polycarbonates, polyacrylonitriles, polyanilines, polyvinyl carbazoles, polyvinyl chlorides, polyvinyl fluorides, polyvinyl imidazoles, polyvinyl alcohols, polystyrenes and poly(vinyl phenols), aliphatic polyesters, polyacrylates, polymethacrylates, acylsutostituted cellulose acetates, nonbiodegradable polyurethanes, polystyrenes, chlorosulphonated polyolefins, polyethylene oxides, polytetrafluoroethylenes, polydialkylsiloxanes, and shape-memory materials such as poly(styrene-block-butadiene), copolymers or mixtures thereof.

In addition to the above materials thermoset or thermoplastic polymers or polymer resins, elastomers, or mixtures thereof may be used for the flexible trial plate base material which include those wherein the polymer or polymer resin contains an aromatic or heteroaromatic moiety, for example, phenyl, biphenyl, pyridinyl, bipyridinyl, naphthyl, pyrimidinyl, including derivative amides or esters of terephthalic acid or naphthalic acid. Examples include those where the polymer or polymer resin comprises polyester, polyamide, polyethylene, polypropylene, polyethylenenaphthalate (PEN), polyethylene terephthalate (PET), polybutylene terephthalate (PBT), polyether etherketone (PEEK), polyamide, polyaryletherketone (PAEK), polyethersulfone (PES), polyethyleneimine (PEI), poly (p-phenylene sulfide) (PPS), polyvinyl chloride (PVC), fluorinated or perfluorinated polymer (such as a polytetrafluoroethylene (PTFE or TEFLON®), polyvinylidene difluoride (PVDF), a polyvinyl fluoride (PVF or TEDLAR®)).

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A kit comprising:
   one or more flexible trial plates formed of a flexible plastic material, at least one of said one or more flexible trial plates comprises at least two guides;
   wherein a region of said one or more flexible trial plates surrounding each of said at least two guides has a different level of radiopacity than the other regions of said one or more flexible trial plates; and
   an insert configured as a spacer, wherein said insert is configured to connect to at least one of said one or more flexible trial plates at a portion between said at least two guides.

2. The kit of claim 1 wherein the at least two guides are at least one of positioning guides and edge markers; and, each having at least some radiopaque portions.

3. The kit of claim 1 wherein the at least two guides are surrounded by radiopaque guide regions.

4. The kit of claim 1 wherein at least one trial plate comprises at least one radiolucent region.

5. The kit of claim 1 wherein the at least one flexible trial plate is coated with a radiopaque material.

6. The kit of claim 1 wherein at least two of the flexible trial plates have different size, shape, or both relative to each other.

7. The kit of claim 6 wherein at least a portion of each of the at least two flexible trial plates is radiopaque.

8. The kit of claim 6 wherein at least a portion of each of the at least two flexible trial plates is radiopaque and at least a portion of each is radiolucent.

9. The kit of claim 1 wherein the at least one flexible trial plate is formed of plastic having radiopaque material therein.

10. The kit of claim 1, wherein said insert is an intervertebral insert.

11. The kit of claim 1, wherein said insert is at least partially radiopaque.

12. The kit of claim 11, wherein at least one of said one or more flexible trial plates comprise a radiolucent portion through which said insert is visible.

13. The kit of claim 1, wherein at least one of said one or more flexible trial plates comprise a radiolucent portion through which said insert is visible, wherein said insert is configured to connect to said radiolucent portion.

14. A flexible trial plate comprising:
a trial plate formed of a flexible plastic material, said trial plate comprising edges, wherein at least some of said edges comprise edge markers comprising a different level of radiopacity than the other regions of said trial plate; and
guides are provided thereon, wherein a region of said trial plate surrounding each of said guides has a different level of radiopacity than the other regions of said trial plate, wherein said edge markers are spaced apart from said region of said trial plate surrounding each of said guides and cover less than an entire one of said edges of said trial plate.

15. The flexible trial plate of claim 14 wherein there are at least two positioning guides surrounded by radiopaque guide regions.

16. The flexible trial plate of claim 14 wherein the flexible trial plate comprises at least one radiolucent region.

17. The flexible trial plate of claim 14 wherein flexible trial plate is coated with a radiopaque material.

18. The flexible trial plate of claim 16 wherein the trial plate is configured wherein at least a portion of a radius is visible, under X-rays or fluoroscope, through the radiolucent region.

* * * * *